United States Patent
Crawford et al.

(10) Patent No.: US 11,987,837 B2
(45) Date of Patent: May 21, 2024

(54) NUCLEIC ACID SEQUENCE ENRICHMENT BY DEFINED NUCLEIC ACID-DIRECTED ENDONUCLEASE DIGESTION

(71) Applicant: CZ Biohub SF, LLC, San Francisco, CA (US)

(72) Inventors: Emily D. Crawford, San Francisco, CA (US); Jenai Quan, San Francisco, CA (US)

(73) Assignee: CZ Biohub SF, LLC, San Francisco, CA (US)

( * ) Notice: Subject to any disclaimer, the term of this patent is extended or adjusted under 35 U.S.C. 154(b) by 464 days.

(21) Appl. No.: 17/265,499

(22) PCT Filed: Aug. 6, 2019

(86) PCT No.: PCT/US2019/045352
§ 371 (c)(1),
(2) Date: Feb. 2, 2021

(87) PCT Pub. No.: WO2020/033438
PCT Pub. Date: Feb. 13, 2020

(65) Prior Publication Data
US 2021/0198719 A1    Jul. 1, 2021

Related U.S. Application Data

(60) Provisional application No. 62/715,180, filed on Aug. 6, 2018.

(51) Int. Cl.
*C12Q 1/6806* (2018.01)
*C12Q 1/6855* (2018.01)

(52) U.S. Cl.
CPC ......... *C12Q 1/6806* (2013.01); *C12Q 1/6855* (2013.01)

(58) Field of Classification Search
None
See application file for complete search history.

(56) References Cited

FOREIGN PATENT DOCUMENTS

| EP | 3601598 B1 * | 8/2022 | ............ | C12Q 1/6806 |
|----|---|---|---|---|
| WO | 0220852 A1 | 3/2002 | | |
| WO | 2018035062 A1 | 2/2018 | | |

OTHER PUBLICATIONS

Swarts DC, Jinek M. Cas9 versus Cas12a/Cpf1: Structure-function comparisons and implications for genome editing. Wiley Interdiscip Rev RNA.;9(5):e1481. doi: 10.1002/wrna. 1481. Epub May 22, 2018. PMID: 29790280. (Year: 2018).*
Application PCT/US2019/045352 , "International Search Report and Written Opinion", Nov. 5, 2019, 9 pages.
Quan et al., "Flash: A Next-Generation CRISPR Diagnostic for Multiplexed Detection of Antimicrobial Resistance Sequences", BioRixv, Sep. 27, 2018, 36 pages.
Shin et al., "CRISPR-Cas9-Targeted Fragmentation and Selective Sequencing Enable Massively Parallel Microsatellite Analysis", Nature Communication, vol. 8, No. 14291, 2017, pp. 1-13.
Slesarev et al., "Crispr/Cas9 Targeted Capture or Mammalian Genomic Regions for Characterization by NGS", BioRxiv, 2018, 36 pages.
Appleby et al., New Technologies for Ultra-High Throughput Genotyping in Plants, Methods in Molecular Biology, vol. 513, Feb. 2009, pp. 19-39.
Drmanac et al., Human Genome Sequencing Using Unchained Base Reads on Self-Assembling DNA Nanoarrays, Science, Reports, vol. 327, No. 5961, Jan. 1, 2010, pp. 78-81.
English et al., Mind the Gap: Upgrading Genomes with Pacific Biosciences RS Long-Read Sequencing Technology, Public Library of Science One, vol. 7, No. 11, Nov. 2012, pp. 1-12.
Fox et al., Applications of Ultra-High-throughput Sequencing, Methods in molecular biology, vol. 553, Feb. 2009, pp. 79-108.
Guha et al., Applications of Alternative Nucleases in the Age of CRISPR/Cas9, International Journal of Molecular Sciences, vol. 18, No. 12, Nov. 2017, pp. 1-13.
Imelfort et al., De Novo Sequencing of Plant Genomes Using Second-generation Technologies, Briefings in Bioinformatics, vol. 10, No. 6, Nov. 2009, pp. 609-618.
Kim et al., A Guide to Genome Engineering with Programmable Nucleases, Nature Reviews Genetics, vol. 15, No. 5, Apr. 2, 2014, pp. 1-14.
Margulies et al., Genome Sequencing in Microfabricated High-Density Picolitre Reactors, Nature, vol. 437, No. 7057, Jul. 2005, pp. 376-380.
Morozova et al., Applications of Next-generation Sequencing Technologies in Functional Genomics, Genomics, vol. 92, No. 5, Nov. 2008, pp. 255-264.
Oyola et al., Whole Genome Sequencing of Plasmodium Falciparum from Dried Blood Spots Using Selective Whole Genome Amplification, Malaria Journal, vol. 15, No. 597, Dec. 2016, pp. 1-12.
Ronaghi et al., Real-Time DNA Sequencing Using Detection of Pyrophosphate Release, Analytical Biochemistry, vol. 242, Nov. 1996, pp. 84-89.

(Continued)

*Primary Examiner* — Nancy J Leith
*Assistant Examiner* — Jessica D Parisi
(74) *Attorney, Agent, or Firm* — Kilpatrick Townsend & Stockton LLP

(57) ABSTRACT

A method of sample analysis is described comprising providing a sample comprising a plurality of endblocked polynucleotides, digesting the sample with one or more defined nucleic acid-directed endonuclease that targets a sequence of interest to produce a digested sample of polynucleotide fragments, wherein one or more of the fragments in the digested sample comprises: a sequence of interest and at least one ligatable end that has been generated by endonuclease cleavage; (c) enriching for fragments that contain the sequence of interest, wherein the one or more sequences of interest are enriched greater than 55 times, or greater than 750 times, their relative abundance in the sample; and (d) analyzing the enriched sample.

14 Claims, 7 Drawing Sheets

(56) References Cited

OTHER PUBLICATIONS

Shendure et al., Accurate Multiplex Polony Sequencing of an Evolved Bacterial Genome, Science, vol. 309, No. 5741, Sep. 9, 2005, pp. 1728-1732.

Zetsche et al., Cpf1 Is a Single RNA-Guided Endonuclease of a Class 2 CRISPR-Cas System, Cell, vol. 163, No. 3, Oct. 2015, pp. 759-771.

Zhao et al., Programmable DNA-Guided Artificial Restriction Enzymes, American Chemical Society Synthetic Biology, vol. 6, No. 5, May 2017, pp. 752-757.

* cited by examiner

NUCLEIC ACID SEQUENCE ENRICHMENT BY DEFINED NUCLEIC ACID-DIRECTED ENDONUCLEASE DIGESTION

FIELD OF THE INVENTION

The present invention relates to the field of nucleic acid sample analysis, particularly to methods for enriching sequences of interest in a nucleic acid sample.

CROSS-REFERENCE TO RELATED APPLICATIONS

This application is a national phase application of PCT Application No. PCT/US2019/045352, filed Aug. 6, 2018, which claims the benefit of U.S. provisional application No. 62/715,180, filed on Aug. 6, 2018, the entire contents of which are incorporated by reference herein.

BACKGROUND

Current methods for enriching sequences of interest in a complex nucleic acid library often involve either multiplex PCR or hybridization to labeled oligonucleotides. These methods can be inefficient, difficult to implement, expensive to optimize, and limited in the number of sequences that can be enriched for in a given sample. Crawford et al. described an alternative method ("FLASH") in which a programmable endonuclease is used to prepare a library enriched in target sequences. See International Patent Application WO2018035062A1.

BRIEF SUMMARY OF THE DISCLOSURE

Described herein is a method that uses a sequence-specific nuclease, such as CRISPR/Cas9, to cut specific sequences of interest in a DNA or other nucleic acid sample prior to sequencing or other molecular analysis applications. In some implementations, the newly exposed ends of the DNA are then free to be ligated to specific adapter sequences that allow them to be amplified. In these embodiments, a single PCR step using only a pair of primers specific to the adaptors can amplify thousands of different sequences, in a fully definable way. To reduce enrichment of non-targeted sequences, the ends of the DNA molecules in the nucleic acid source may be end-blocked, e.g., treated with a phosphatase or using another method, prior to nuclease digestion to block any already accessible DNA ends. The method described herein can result in 100, 1,000, 10,000 or 100,000-fold enrichments of sequences of interest.

In some embodiments, the method may comprise: (a) providing a sample comprising a plurality of end-blocked polynucleotides; (b) digesting the sample with one or more sequence specific endonuclease that targets a sequence of interest to produce a digested sample of polynucleotide fragments, wherein one or more of the fragments in the digested sample comprises: (i) a sequence of interest and (ii) at least one ligatable end that has been generated by endonuclease cleavage; (c) enriching for fragments that contain the sequence of interest, wherein the one or more sequences of interest are enriched greater than 55 times their relative abundance in the sample; and (d) analyzing the enriched sample. In some embodiments the nucleic acid-directed endonuclease is a defined nucleic acid-directed endonuclease. In some embodiments the nucleic acid-directed endonuclease is a Cas protein-guide nucleic acid (e.g., RNA) complex.

In some embodiments fragments with at least two ligatable ends are generated by endonuclease cleavage. In various embodiments the method is carried out using a total quantity of end-blocked polynucleotides in the range 10 picograms to 100 nanograms. In various embodiments the method is carried out using total quantity of programmed endonuclease (e.g., Cas9) that is in the range 0.0032 pmole to 2 pmoles per nanogram DNA. In various embodiments the endonuclease (e.g., Cas9) is inactivated using a protease (e.g., Proteinase K). In various embodiments, following inactivation of the endonuclease by protease digestion, the polynucleotide fragments are separated from protease. In some embodiments, following inactivation of the endonuclease, the polynucleotide fragments are separated from catalytically active protease. In various embodiments, following inactivation of the endonuclease by protease digestion, the polynucleotide fragments are separated from proteins, including protease, in the reaction mixture (i.e., the polynucleotide products are partially purified). In some embodiments, following endonuclease digestion the polynucleotide fragments are not exposed to elevated temperature. Examples of elevated temperature include 55° C. or higher, 65° C. or higher, 75° C. or higher, 85° C. or higher, 90° C. or higher, or 95° C. or higher for more than 0 seconds, for more than 10 seconds, or for more than 30 seconds. In some embodiments, following endonuclease digestion the polynucleotide fragments are not exposed to conditions of temperature and time that inactivate proteases (e.g., Proteinase K) in the reaction mixture.

In one aspect, a method of sample analysis is described, comprising: (a) providing a sample comprising a plurality of end-blocked polynucleotides; (b) digesting the sample with one or more defined nucleic acid-directed endonuclease that targets a sequence of interest to produce a digested sample of polynucleotide fragments, wherein one or more of the fragments in the digested sample comprises: a sequence of interest and at least one ligatable end that has been generated by endonuclease cleavage; (c) enriching for fragments that contain the sequence of interest, wherein the one or more sequences of interest are enriched greater than 55 times their relative abundance in the sample; and (d) analyzing the enriched sample. In some embodiments the method comprises ligating an adaptor to ligatable ends generated by endonuclease digestion (cleavage) step. Methods and strategies for addition of adaptors are well known and may be carried out using any suitable ligase (including, e.g., T4 DNA ligase, T3 DNA ligase, and T7 DNA ligase). In some embodiments the digesting step creates fragments with ligatable endonuclease cleavage sites on each end, and the method comprises ligating adaptors to each end of the fragments. In some embodiments the enriching comprises amplifying the ligated fragments using primers that hybridize to the adaptors, or complements thereof. In some embodiments the adaptor comprises capture moiety and the enriching is done by binding the capture moiety to a support, and washing away the unbound nucleic acid. In some embodiments the adaptors comprise a molecule indexer. In some embodiments the endonucleases digestion produces fragments of a defined size range and optionally the enriching comprises size selection of the fragments.

In various embodiments the ligatable ends generated by endonuclease treatment are blunt ends. In various embodiments the endonuclease is Cas9, Argonaute, an ortholog thereof, or a variant thereof. In various embodiments the sample is digested by at least two defined nucleic acid-directed endonucleases.

In some embodiments the method comprises ligating indexed adaptors to each end of the fragments where the index comprises a series of random nucleotides of sufficient length such that there is at least about 95% probability of each fragment receiving a distinct index, sequencing the ligated fragments to produce sequence reads, and counting the number of molecule indexer sequences that are associated with a sequence of interest in the sequence reads, thereby providing an estimate of the copy number of the sequence of interest in the nucleic acid sample.

In an embodiment the method further comprises, providing a sample comprising a plurality of end-blocked polynucleotides; separately digesting a first portion of the sample with one or more defined nucleic acid-directed endonuclease that targets a sequence of interest to produce a first digested sample of polynucleotide fragments, wherein one or more of the fragments in the digested sample comprises, a first sequence of interest and at least one ligatable end that has been generated by endonuclease cleavage; a second portion of the sample with one or more defined nucleic acid-directed endonuclease that targets a sequence of interest to produce a second digested sample of polynucleotide fragments, wherein one or more of the fragments in the digested sample comprises a second sequence of interest and at least one ligatable end that has been generated by endonuclease cleavage and wherein at least some of the fragments in the first digested sample overlap with at least some of the fragments in the second digested sample; enriching for fragments that comprise the sequences of interest; sequencing the enriched sequences to produce a plurality of sequence reads; and assembling overlapping sequence reads, thereby obtaining a contiguous sequence of a first sequence of interest and a second sequence of interest. In some embodiments in step (a) the quantity of end-blocked polynucleotides in the sample is in the range of 10 picograms to 100 nanograms and/or in step (b) the amount of nucleic acid-directed endonuclease is in the range 0.0032 pmole to 2 pmoles per nanogram DNA and/or in steps (b) and (c) the sample comprising polynucleotides is not exposed to an elevated temperature. In some embodiments the analyzing of (d) comprises sequencing. In some embodiments the sample is digested by at least two defined nucleic acid-directed endonucleases.

In some embodiments the nucleic acid sample comprises DNA from at least two organisms. In some embodiments, the at least two organisms comprise a mammal and a pathogen (e.g., virus, bacteria or fungus) or a mammal and a microbiome. In some embodiments the mixed sample comprises (i) wild type and mutant DNA; (ii) a clinical sample; (iii) a bodily fluid or excretion; (iv) blood, sputum, or feces; (v) a tumor biopsy; an environmental sample, a sample from a crime scene or an archaeological sample.

DETAILED DESCRIPTION OF THE DISCLOSURE

Next generation sequencing (NGS) encompasses a powerful collection of technologies. In some applications it is desirable to prepare a sequencing library enriched for nucleic acid sequences of interest, especially low abundance sequences in a complex mixture. The present invention is an improved variation of the FLASH method described in International Published Patent Application WO2018035062A1, published Feb. 22, 2018, which is incorporated herein by reference. Using the methods described herein (sometimes referred to as "enrichment-plus-NGS"), enrichment of sequences of interest to greater than 800 times their relative abundance in starting sample may be achieved.

In one approach input genomic DNA or cDNA is first blocked by phosphatase treatment and then digested with Cas9 complexed to a set of guide RNAs. The resulting cleavage products are thus made competent for ligation of universal sequencing adapters. With the ensuing amplification, the targeted sequences are enriched over background and made ready for binding to the sequencing flow cell. This method goes beyond other CRISPR-based diagnostic tools in that it enables high levels of multiplexing (thousands of targets) and is reinforced by the precision and sequence identity confirmation that is inherent in a traditional NGS readout. The Examples highlight uses of enrichment-plus-NGS in the realm of drug resistant infections (e.g., antimicrobial resistance genes in pneumonia-causing gram-positive bacteria and drug resistance in the malaria parasite *Plasmodium falciparum*).

Selected elements of the enrichment-plus-NGS method are described in Quan et al., "FLASH: A next-generation CRISPR diagnostic for multiplexed detection of antimicrobial resistance sequences," published September 2018 in bioRxiv 426338, which is incorporated herein by reference for all purposes.

1. PROTOCOL OVERVIEW

Figure 1:
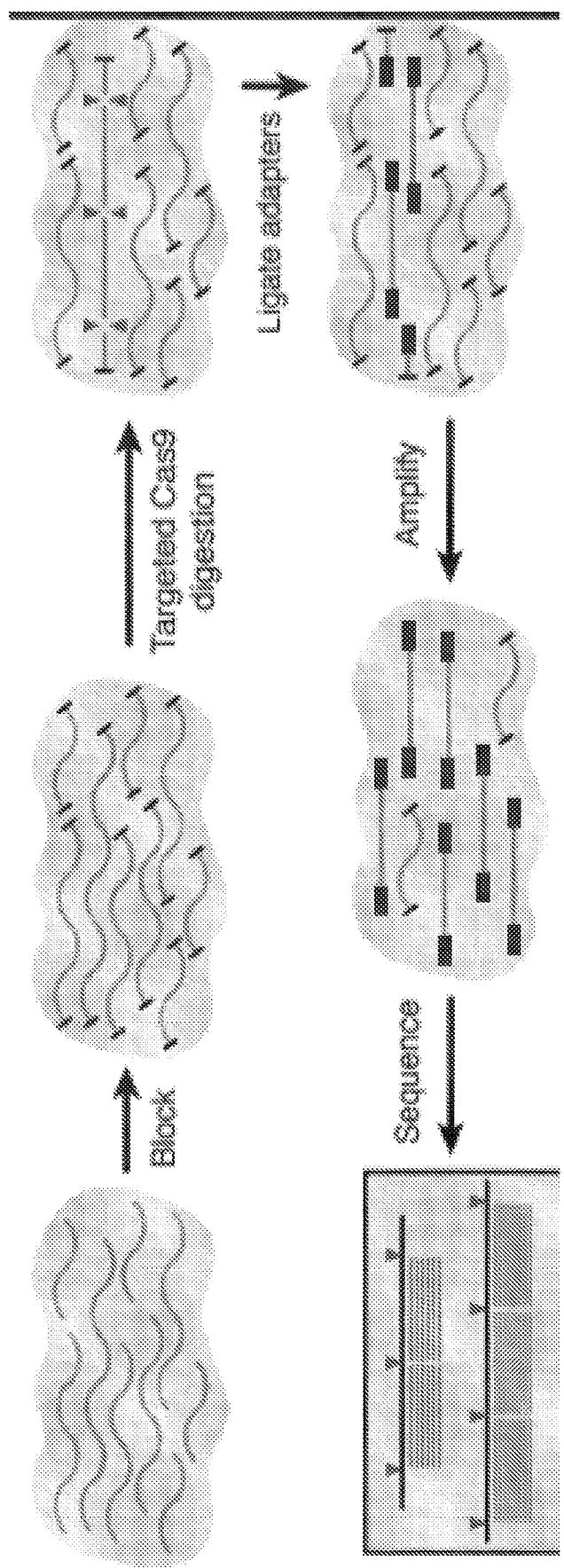
FIG. 1 shows a schematic of the general enrichment method described herein. Step 1: Obtain nucleic acid sample; Step 2: End-blocked nucleic acid sample; Step 3: End-blocked nucleic acid sample digested at sequences of interest by defined endonuclease; Step 4: Enrich for sequences of interest (e.g., by adaptor ligation and/or size selection); and Step 5: Analyze (e.g., by next-generation sequencing).

FIG. 1 shows a schematic of one version of the method. As will be apparent, certain steps of the method may be done in vitro, i.e., in a cell-free environment using isolated nucleic acid (e.g., isolated DNA). The method comprises providing a sample comprising a plurality of end-blocked polynucleotides. The end-blocked nucleic acid sample digested at sequences of interest by defined endonuclease (also called a programmable endonuclease) such as Cas9 or variants. The enrichment method described herein is definable in that it can be applied to a user-defined set of sequences of interest. For example, any sequence for which a suitable guide RNA can be designed can be targeted for enrichment by Cas9 digestion using this method. The endonuclease-produced fragments enriched by preferential amplification. In one approach the amplification comprises ligation of adaptors to the unblocked ends produced by endonuclease cleavage and amplification of sequences flanked by adaptors and/or present on a fragment comprising an adaptor sequence. The library comprising the enriched fragments is analyzed, usually by DNA sequencing.

2. END BLOCKED DNA SAMPLES

The starting sample DNA may be DNA from any source or combination of sources, including genomic DNA (gDNA), complementary DNA (cDNA), or mitochondrial mDNA. The DNA may be randomly fragmented, such as randomly fragmented genomic DNA derived from patient samples and randomly fragmented cDNA libraries derived from patient samples. Other examples of nucleic acid suitable for analysis according to the invention are described below in Section 9, below.

The method may comprise end-blocking nucleic acid fragments in the nucleic acid sample (e.g., mixed nucleic acid sample) prior to endonuclease digestion, so that the ends of the nucleic acid fragments are not available for ligation. In one approach, prior to endonuclease digestion, the method may comprise treating the nucleic acid sample with a phosphatase thereby removing the 5' phosphate groups from the nucleic acid in the sample and making the 5' ends of the nucleic acid in the sample unligatable. Exemplary phosphatases that may be used include calf intestinal phosphatase (CIP), shrimp alkaline phosphatase (SAP), placental alkaline phosphatase (PLAP) or secreted embryonic alkaline phosphatase (SEAP).

Alternative blocking methods are also possible, including ligation of a hairpin adaptor, ligation of an adaptor containing a chemical blocking group, ligation of an adaptor lacking a 5' phosphate, chemical addition of a blocking group, enzyme-mediated addition of a modified nucleotide, enzyme-mediated addition of one or more nucleotides producing a sticky end overhang that is incompatible with the future ligation of the a specific adaptor, or any other method that prevents efficient downstream ligation of a functional adaptor.

As used herein, references to a quantity (e.g., weight in nanograms) of "sample DNA" refers to the quantity of DNA in a sample prior to an end-blocking step. That is, unless specified otherwise, if a sample of 100 ng of DNA (e.g., from a patient) is treated with phosphatase, the resulting product is considered to be a 100 ng sample comprising a plurality of end-blocked polynucleotides, without regard to whether any DNA is lost during an end-blocking process. It is contemplated that usually no more than 10% of sample DNA may be lost during end-blocking and associated cleanup.

3. DIGESTION USING DEFINED NUCLEIC ACID-DIRECTED ENDONUCLEASE

The method comprises digesting a nucleic acid sample with a plurality of defined nucleic acid-directed endonucleases (also called "programable endonucleases") that target sequences of interest (e.g., a set of Cas9 endonuclease, Argonaut, ortholog or variant of the same that have synthetic guide RNAs or DNAs that target the endonucleases to defined target sites in a target nucleic acid, e.g., a target genome). "Plurality" in this context means a plurality of endonuclease-nucleic acid complexes, comprising one or more endonuclease proteins associated with a large library of associated nucleic acids. Digestion of the nucleic acid sample with the nucleic-acid directed endonucleases produces a digested sample that contains fragments of the nucleic acid in the sample, where at least some of the fragments in the digested sample contain: (i) a sequence of interest and (ii) at least one ligatable end that has been generated by endonuclease cleavage (i.e., an end that contains a 5' phosphate and a 3' hydroxyl, where the end is blunt or has a defined overhang). A ligatable end may be capable of acting as a substrate for ligation by T4 DNA ligase. Some nucleic acid-directed endonucleases, including Cas9, generate blunt ends, whereas others produce may produce defined overhangs.

3.1 ENDONUCLEASE

Any suitable programable endonuclease may be used in this method. A "programmable" endonuclease is a nucleic acid-protein complex that cleaves double stranded DNA in a sequence specific fashion where the specificity is determined by the sequence of the nucleic acid component. As used herein, reference to a nucleic acid-directed endonuclease (e.g., Cas) will be understood to mean an endonuclease-guide nucleic acid complex. Typically the endonuclease is a CRISPR-associated (Cas) protein. Examples include Cas9 (discussed below) Cas12 (Cpf1), PfAgo (Argonaute) and variants and orthologs of each. In some embodiments a sequence-specific nuclease other than CRISPR associated protein or other than a programable endonuclease (as defined above) is used. Examples include TALENS and Zinc Finger Nucleases, meganucleases and other highly sequence-specific nucleases. For illustration and not limitation, endonucleases that may be used in the enrichment-plus-NSG methods are described in Zetsche et al., 2015, *Cell.* 163(3):759-71; Enghiad and Zhao, 2015, *ACS Synth. Biol.* 65:752-757; Kim et al., 2014, *Nat Rev Genet.* 15:321-34; and Guha et al., 2017, *Int. J. Mol. Sci.* 18:2565 each of which is incorporated herein by reference for all purposes.

In some embodiments the endonuclease is *Streptococcus pyogenes* Cas9 protein, or ortholog or variant thereof. A Cas9 protein may be at least 60% identical (e.g., at least 70%, at least 80%, or 90% identical, at least 95% identical or at least 98% identical or at least 99% identical) to a wild type Cas9 protein, e.g., to the *Streptococcus pyogenes* Cas9 protein. The Cas9 protein may have all the functions of a wild type Cas9 protein, or only one or some of the functions, including binding activity, and nuclease activity.

For Cas9 to successfully bind to DNA, the target sequence in the genomic DNA should be complementary to the gRNA sequence and is usually immediately followed by the correct protospacer adjacent motif or "PAM" sequence. The PAM sequence is present in the DNA target sequence but not in the gRNA sequence. Any DNA sequence with the correct target sequence followed by the PAM sequence will be bound by Cas9. The PAM sequence varies by the species of the bacteria from which Cas9 was derived. The most widely used Type II CRISPR system is derived from *S. pyogenes* and the PAM sequence is NGG located on the immediate 3' end of the gRNA recognition sequence. The PAM sequences of Type II CRISPR systems from exemplary bacterial species include: *Streptococcus pyogenes* (NGG), *Neisseria meningitides* (NNNNGATT), *Streptococcus thermophilus* (NNAGAA) and *Treponema denticola* (NAAAAC). With some other sequence-specific nucleases, such as Argonauts, a PAM site is not required for binding and cutting the target DNA.

3.2 GUIDE RNAs

For Cas9, the guide RNAs may be composed of two molecules, i.e., one RNA ("crRNA") which hybridizes to a target and provides sequence specificity, and one RNA, the "tracrRNA", which is capable of hybridizing to the crRNA. Alternatively, the guide RNA may be a single molecule (i.e., a sgRNA) that contains crRNA and tracrRNA sequences.

The guide RNAs used in the method may be designed so that they direct binding of the endonuclease to predefined cleavage sites in a target genome(s), for example. In certain cases, the cleavage sites may be chosen so as to release a fragment that contains a region of unknown sequence, or a region containing a SNP, nucleotide insertion, nucleotide deletion, rearrangement, etc. Since genomic isolation methods, and the nucleotide sequences of many organisms (including many bacteria, fungi, plants and animals, e.g., mammals such as human, primates, and rodents such as mouse and rat) are known, designing guide RNAs for use in the present method should be within the skill of one of skilled in the art. For example, Cas9-gRNA complexes can be programmed to bind to any sequence, provided that the sequence has a PAM motif. In theory, the Cas9-gRNA complexes could cleave the genomic DNA to produce fragments in the range of 30-50 bp. However, in practice, the minimal interval between the cleavage sites may be e.g., in the range of 50-900 bp. In some embodiments, the sgRNA or crRNA can be a degenerate sequence to target relatively conserved regions.

3.3 MULTIPLEXING GUIDE RNAS

The method may make use of a set of at least 2, at least 5, at least 10, at least 100, at least 1,000, at least 10,000, at least 50,000 or at least 100,000 or more different guide RNAs/DNAs that are each complementary to a different, defined, site in one or more genomes. The distance between neighboring sites may vary greatly depending on the desired application. In some embodiments, the distance between neighboring sites may be in the range of 100 bp to 200 kb, and, in particular embodiments, the sites may be chosen to release fragments that are within a defined, size range, e.g., 100 bp to 2 kb, e.g., 200 bp to 1 kb for example, or larger (e.g., 500 bp to 20 kb). Large fragments may be suited for use in nanopore and/or PacBio sequencing. In certain cases, the guide RNAs/DNAs may be may be chosen to release fragments that are of a size (e.g., less than 1 kb or less than 500 bp) that are suitable for size selection. In these embodiments, the fragments may be less than 1 kb in length or longer than about 1 kb in length and the enriching may be done by size selecting the fragments. In some embodiments, one guide RNA/DNA may be chosen for one target gene of interest. In other embodiments, a plurality of guide RNAs/DNAs may be chosen for one target gene of interest.

4. ENRICHMENT AND AMPLIFICATION

As noted above, the enrichment-plus-NGS method uses a sequence-specific nuclease to cut sample DNA at sequences of interest, generating fragments with newly exposed ends of the DNA. The exposed ends are then free to be ligated to specific adapter sequences that allow them to be amplified. In these embodiments, a single PCR step using only a pair of primers specific to the adaptors can therefore amplify hundreds to millions of different sequences, in a fully definable way. In some embodiments, digestion by the endonuclease may produce fragments that have two ends, both of which are ligatable. In these embodiments, the method comprises ligating adaptors to both ends of the fragments, thereby allowing the ligated fragments to be enriched by PCR using a single pair of primers that hybridize to the adaptors, or complements thereof. In these embodiments, the fragments can also be enriched by size, before or after they are ligated to the adaptors. As would be apparent, the adaptor used should be compatible with the ends generated by the endonuclease. In some embodiments, the end of the adaptor that is ligated to the fragments may be blunt-ended. In other embodiments, the end of the adaptor that is ligated to the fragments may have an overhang that is complementary to the overhang generated by the endonuclease. In further embodiments, blunt-ended fragments may be A-tailed (e.g., using Taq polymerase) prior to ligation to a T-tailed adaptor. As noted above, in some embodiments, the adaptor may be a Y-adaptor and, as such, each strand of a ligation product may by asymmetrically tagged in that it has the sequence of one strand of the Y-adaptor at one end and the other strand of the Y-adaptor at the other end, where the added sequences are not the same or complementary. Amplification of nucleic acid molecules that have been joined to Y-adaptors at both ends results in an asymmetrically tagged nucleic acid, i.e., a nucleic acid that has a 5' end containing one tag sequence and a 3' end that has another tag sequence. Thus, after digestion, fragments that contain the sequence of interest can be enriched, e.g., using size selection, by ligating an adaptor that comprises a capture moiety (e.g., a biotin moiety) to the ligatable end generated by the endonuclease, binding the capture moiety to a support (e.g., a streptavidin support), and washing away the unbound nucleic acid, or by ligating adaptors (e.g., "Y-adaptors") to the ends of the fragments and amplifying the ligated fragments by PCR using primers that bind to or are complementary to sequences in the Y adaptors.

5. ENRICHMENT-PLUS-NGS MAY BE CARRIED OUT USING A VERY SMALL AMOUNT OF END-BLOCKED NUCLEIC ACID

The starting sample DNA may be cDNA or gDNA. Surprisingly, this protocol may be applied to starting amounts of as little as 100 femtograms of sample DNA. Preferably the amount of sample DNA ranging to start is in the range from 10 picograms to 100 nanograms, e.g., 10 picograms to 1 nanogram, or 1 nanogram to 100 nanograms.

6. THE RELATIVE AMOUNTS OF ENDONUCLEASE AND END-BLOCKED DNA (E.G., CAS9) CRITICALLY AFFECT RESULTS

We have discovered that, surprisingly, carrying out the 'FLASH' enrichment-plus-NGS method using a very small quantity of programable endonuclease (e.g., Cas9) per quantity of DNA sample strikingly improves the level of enrichment of target DNA. See Example 4. In various embodiments the amount of endonuclease (e.g., Cas9) used is not more than about 2 pmole/ng sample DNA, preferably not more than about 1 pmole/ng DNA, more preferably not more than 0.5 pmole/ng DNA and most preferably about 0.4 pmole endonuclease (e.g., Cas9) /ng DNA. In general, the amount of nucleic acid directed endonuclease is not more than about 2 pmole/ng sample DNA, preferably not more than about 1 pmole/ng DNA, more preferably not more than 0.5 pmole/ng DNA and most preferably 0.4 pmole endonuclease (e.g., Cas9)/ng DNA. In some embodiments the amount of Cas9 or other endonuclease is in the range of 0.0000256 pmole to 10 pmoles, preferably 0.0000256 to 2 pmoles, most preferably 0.0032 pmole to 2 pmoles. In some embodiments the amount of Cas9 or other endonuclease used per ng DNA has a lower limit of 0.0000256, 0.000128, 0.00064, 0.0032, 0.016, or 0.08 pmoles and an upper limit of 0.16, 0.08, 0.4 or 2 pmoles where the upper limit is greater than the lower limit Without intending to be limited to a particular embodiment, Cas9 is typically purified from bacteria, for example, *Escherichia coli* (*E. coli*). As such, Cas9 is often purified alongside DNA from the *E. coli* cell. This *E. coli* DNA may comprise at least one ligatable end that may be enriched in the methods described herein and thus function as non-sample DNA that may be inadvertently enriched in the methods described herein.

When a programable endonuclease other than Cas9 is used, a preferred amount or range of enzyme can be determined as described in Example 8. In general the amount of endonuclease is 10 pmole endonuclease, or less, per ng DNA.

In an alternative approach Cas9 is substantially free of non-sample DNA.

7. REMOVAL OF ENDONUCLEASE

After digestion (and optionally after amplification), the residual endonuclease may be inactivated or removed. In one approach, a protease is added to digest and thereby inactivate the Cas9 protein or other programmable endonuclease. Any number of proteases may be used (e.g., trypsin, chymotrypsin, thermolysin). In one embodiment the protease is Proteinase K.

Figure 2:
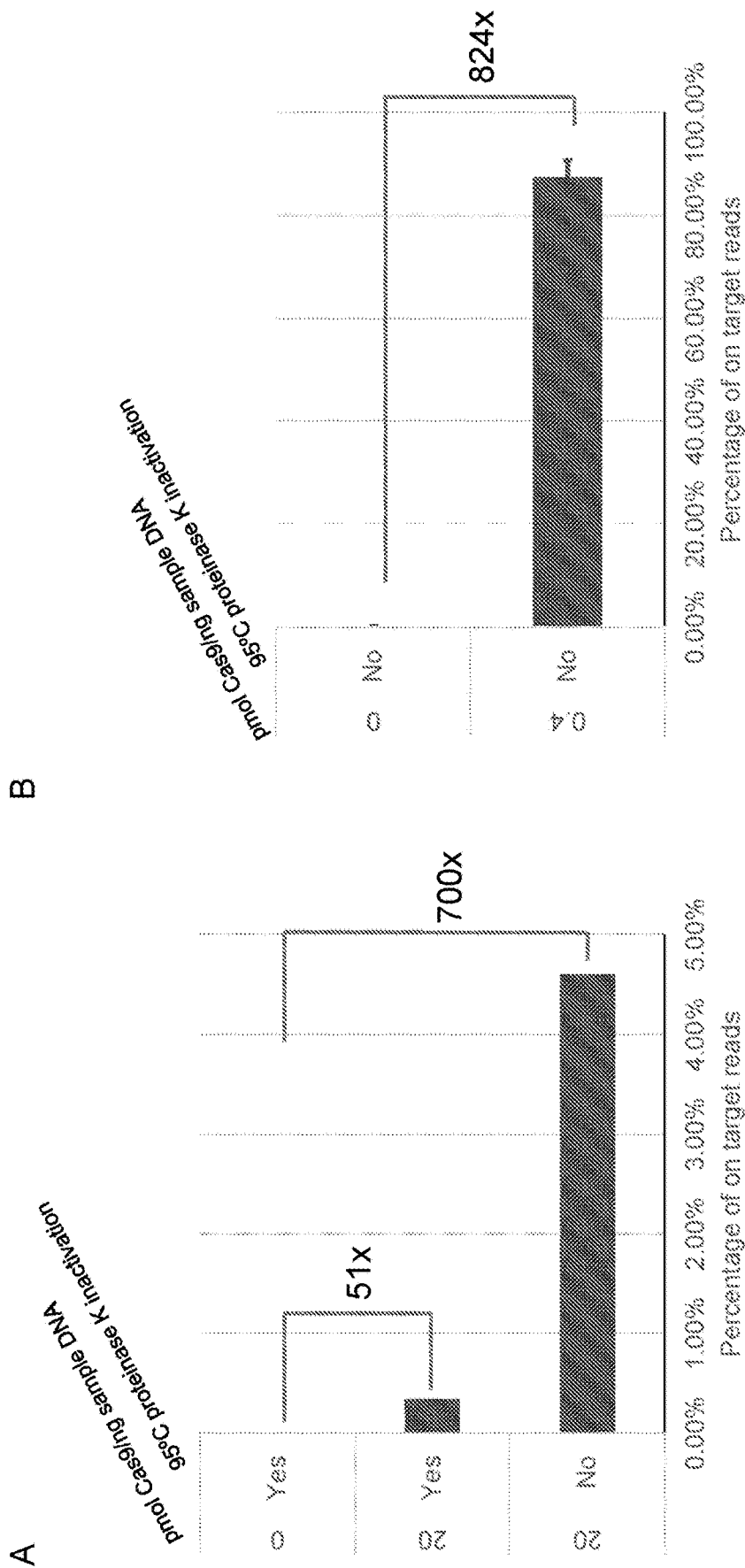
FIG. 2A and 2B show that removing the heat inactivation step increased the percentage of on-target reads (from <0.5% to >4.5% when 20 pmole Cas9 per ng sample DNA is used. See FIG. 2A. Reducing the concentration of Cas9 (from 20 pmol Cas9/ng sample DNA to 0.4 pmol Cas9/ng sample DNA) resulted in an increase of the percentage of on-target reads (from <5% to >80%). Compare FIG. 2A and FIG. 2B.

Conventionally, Proteinase K and other protease are inactivated by heat, e.g., incubation at 95 degrees C. However, we have discovered that, surprisingly, superior results are observed when the digested sample nucleic acid is can be purified away from proteinase K through methods that do not require incubation at 95 degrees C. See Examples 2 and 3, and FIGS. 2A and 2B, showing the percentage of on-target reads following the method of enrichment described herein applied to Plasmodium samples. In one approach DNA binding solid phase reversible immobilization (SPRI) beads are used to separate DNA and protease.

In some embodiments, following inactivation of the endonuclease by enzymatic digestion, the polynucleotide fragments are separated from catalytically active protease. In some embodiments following endonuclease digestion the polynucleotide fragments are not exposed to elevated temperature. Examples of elevated temperature include 55° C. or higher, 65° C. or higher, 75° C. or higher, 85° C. or higher, 90° C. or higher, or 95° C. or higher for more than 0 seconds, for more than 10 seconds, for more than 30 seconds. In some embodiments following endonuclease digestion the polynucleotide fragments are not exposed to conditions of temperature and time that inactivate proteases (e.g., Proteinase K) in the reaction mixture.

8. ENRICHMENT RESULTS

As discussed in the examples, a high level of enrichment of sequences of interest was observed when 0.4 pmol Cas9 was used for every ng of sample DNA input, and when there is no 95 degree C. inactivation of proteinase K. As discussed in the Examples, this method enriches sequences of interest to greater than 800 times their relative abundance in starting sample. In some embodiments, the method used an amount of endonuclease (which may be Cas9, or an ortholog or varient thereof) described in Section 6, above, for every ng of sample DNA input, and when there is no 95 degree C. inactivation of proteinase K. As discussed in the Examples, this method results in enrichment of sequences of interest to greater than 800 times their relative abundance in starting sample.

The present invention provides for the enrichment of sample DNA to facilitate detection and identification of the sample DNA through various conventional techniques. The enrichment of a sequence or sequences of interest in a given sample is at least about 55 X (55 times or 55-fold) their abundance in the sample nucleic acid. In some embodiments, the enrichment is at least about 60 X, 75 X, 100 X, 150 X, 200 X 250 X, 300 X, 400 X, 500 X, 750 X, 1000 X, or 2000 X abundance of the sequence or sequences of interest in the sample nucleic acid. For example, a gene may comprise one or more sequences of interest. The enrichment of a gene of interest in a given sample is at least about 50 X its abundance in the sample nucleic acid. In some embodiments, the enrichment of a gene of interest is at least about 55 X, 100 X, 500 X, 1000 X, 2500 X, 5000 X, 7500 X, 10,000 X, 20,000 X, 50,000 X, 75,000 X, 100,000 X, 250,000 X, 500,000 X, or 1,000,000 X.

As described in Example 5, using the enrichment-plus-NGS method described herein, a sequencing depth of 3000 reads was sufficient to recover 10 or more reads per gene for 100% of targeted genes. In embodiments of the present invention, a sequencing depth less than $10^5$, preferably less than $10^4$ and most preferably a sequencing depth less than $5 \times 10^3$ results in 10 or more reads per target gene. In one embodiment an assay is provided in which programmable endonucleases specific for 10 or more, or 20 or more target genes are used to carry out enrichment-plus-NGS and a sequencing depth of less than $10^5$, preferably less than $10^4$ and most preferably a sequencing depth less than $5 \times 10^3$ results in 10 or more reads for said 10 or 20 targets. In some embodiments the target genes are bacterial genes, optionally gene from pathogenic bacteria. In some embodiments the target genes confer drug resistance to the bacterial. In some embodiments the target genes comprise at least 5 genes selected from the group consisting of mecA, rpoB, mprF, dfrG, parE, gyrB, rpoC, gyrA, parC, mecR1, cls, ErmC, and pgsA.

9. OPTIONAL INDEXING

In some embodiments, the adaptor may contain an index sequence, e.g., a sequence that varies from molecule to molecule, such as a random sequence, thereby allowing molecules to be counted. In these embodiments, the method may comprise ligating an indexed adaptor to both ends of the fragments, amplifying the ligated fragments, sequencing the ligated fragments to produce sequence reads, and then counting the number of molecule indexer sequences that are associated with a sequence of interest in the sequence reads, thereby provide an estimate of the copy number of the sequence of interest in the nucleic acid sample. This allows the user to evaluate the relative quantities of different sequence molecules in the original sample.

10. NEXT GENERATION SEQUENCING

The enriched fragments can be analyzed by any suitable method, e.g., sequencing or mass spectrometry. As would be apparent, the adaptors and/or the primers used for amplification may be compatible with use in any next generation sequencing platform. In one approach in which primer extension is used, e.g., Illumina's reversible terminator method, Roche's pyrosequencing method (454), Life Technologies' sequencing by ligation (the SOLiD platform), Life Technologies' Ion Torrent platform, Complete Genomics' DNB platform, or Pacific Biosciences' fluorescent base-cleavage method. Examples of such methods are described in the following references: Margulies et al (Nature 2005 437:376-80); Ronaghi et al (Analytical Biochemistry 1996 242:84-9); Shendure (Science 2005 309:1728); Imelfort et al (Brief Bioinform. 2009 10:609-18); Fox et al (Methods Mol Biol. 2009;553:79-108); Appleby et al (Methods Mol Biol. 2009;513:19-39) English (PLoS One. 2012 7:e47768); Drmanac et al., 2010, *Science* 327:5961:78-81); and Morozova (Genomics. 2008 92:255-64), which are incorporated by reference for the general descriptions of the methods and the particular steps of the methods, including all starting products, reagents, and final products for each of the steps. Indeed, if the products are amplified on a solid support (e.g., using an Illumina flow cell), then the amplicons may be sequenced in place on the substrate. The sequencing step may be done using any convenient next generation sequencing method and may result in at least 10,000, at least 50,000, at least 100,000, at least 500,000, at least 1 M at least 10 M at least 100 M or at least 1 B sequence reads. In many cases, the reads are paired-end reads.

The

11. OVERLAPPING SEQUENCE READS

The method may be used to obtain overlapping sequence reads, thereby allowing assembly of a contig. In these embodiments, the method may comprise: (a) separately digesting (e.g., in separate containers or separate aliquots): (1) a first portion of the nucleic acid sample with a first plurality of reprogrammed nucleic acid-directed endonucleases that target sequences of interest to produce a first digested sample, wherein at least some of the fragments in the first digested sample comprise: (i) a first sequence of interest and (ii) at least one ligatable end, and preferably two ligatable ends, that has been generated by endonuclease cleavage; (II) a second portion of the nucleic acid sample with a second plurality of reprogrammed nucleic acid-directed endonucleases that target sequences of interest to produce a second digested sample, wherein at least some of the fragments in the second digested sample comprise: (i) a second sequence of interest and (ii) at least one ligatable end, and preferably two ligatable ends, that has been generated by endonuclease cleavage. In this method, the endonucleases in each digestion may be designed so that at least some of the fragments in the first digested sample overlap with at least some of the fragments in the second digested sample, e.g., may have an overlap of at least 50, at least 100 or at least 200 bases). The fragments that contain the sequence of interest may be enriched as described above (e.g., by ligating an adaptor and amplifying the fragments by PCR using primers that hybridize to a sequence in the adaptor, or complement thereof), and then sequenced to produce a plurality of sequence reads. After sequencing, the method may comprise assembling any overlapping sequence reads, thereby obtaining a contig containing the sequence of at least part of the first sequence of interest and at least part of the second sequence of interest.

12. NUCLEIC ACID (E.G. MIXED DNA) BEING ANALYZED

The nucleic acid sample may be collected from any source, including any organism, organic material or nucleic acid-containing substance including, but not limited to, plants, animals (e.g., reptiles, mammals, insects, worms, fish, etc.), tissue samples, bacteria, fungi (e.g., yeast), microbial eukaryotes, phage, viruses, cadaveric tissue, archaeological/ancient samples, etc. In certain embodiments, the genomic DNA used in the method may be derived from a mammal, wherein certain embodiments the mammal is a human.

In some embodiments the nucleic acids being analyzed may be derived from a single source (e.g., from different genes in the same genome or a time course in a single subject), whereas in other embodiments, the nucleic acid sample may be a pool of nucleic acids extracted from a plurality of different sources (e.g., a pool of nucleic acids from different subjects), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. Molecular barcodes may allow the sequences from different sources to be distinguished after they are analyzed.

The nucleic acid sample may be a mixed nucleic acid sample (i.e., a nucleic acid sample that contains DNA from at least two sources, where the DNA from one sources may represent less than 10%, less than 5%, less than 2% or less than 1% of the total DNA in the sample).

In some embodiments, the nucleic acid sample may comprise DNA from at least two organisms. Examples include (A) a mammal and a pathogen (where the pathogen may be a virus, bacterium or fungus, for example), (B) a mammal and a parasite, (C) a mammal and a microbiome, or (D)two microorganisms in a microbiome, where the DNA from one of the organisms may be at least 10 times, at least 50 times, or at least 100 times, at least 500 times, at least 1000 times, or at least 10,000 times more abundant than the other.

In some embodiments, the nucleic acid sample may contain wild type and mutant DNA from the same organism (e.g., a cancer patient). In some approaches the wild-type DNA may be at least 10 times, at least 50 times, or at least 100 times, at least 500 times, at least 1000 times, or at least 10,000 times more abundant than the mutant DNA.

In some embodiments, the nucleic acid sample may contain maternal and fetal DNA, such as circulating cell-free fetal DNA.

In some embodiments, the mixed sample may be an environmental sample, a sample from a crime scene or an archaeological sample. In some embodiments, the mixed sample is made from a clinical sample, e.g., from a patient suspected of having been infected by a pathogen. The clinical sample may a bodily fluid or excretion listed below. In some embodiments, the clinical sample may be a tumor biopsy.

The above described method is useful for the analysis of samples in a variety of diagnostic, drug discovery, and research applications. The above described method is useful for the analysis of biological samples. The term "biological sample," as used herein, refers to a sample obtained from an organism or from components (e.g., cells) of an organism. The sample may be of any biological tissue or fluid. In some cases, the sample will be a "clinical sample" which is a sample derived from a patient. Such samples include, but are not limited to, sputum, blood, blood cells (e.g., white blood cells), tissue or fine needle biopsy samples, urine, peritoneal fluid, and pleural fluid, or cells there from. Biological samples may also include sections of tissues such as frozen sections taken for histological purposes. The subject method also finds use in determining the identity of microbes in water, sewage, air samples, food products, including animals, vegetables, seeds, etc., soil samples, plant samples, microbial culture samples, cell culture samples, tissue culture samples, as well as in human medicine, veterinary medicine, agriculture, food science, bioterrorism, and industrial microbiology, etc. The subject method allows identification of hard to culture microbes since culturing the microbes is not necessary. Consequently, the subject method provides for a rapid detection of microbes in a sample with no waiting period for culturing microbes.

In some embodiments, the method may be employed to identify a microbe (e.g., microbial pathogens) from a clinical sample. In these embodiments, the endonucleases may target sequences from multiple different microbes (e.g., pathogens) (e.g., at least 2, at least 5, at least 10, at least 50 or at least 100 different pathogens). In some embodiments the method is used in a patient with signs or symptoms of microbial pathogen infection, without knowing which pathogen is responsible for an infection, the enriched nucleic acid may be sequenced, and the sequences may be compared to sequences from known pathogens, e.g., bacterial, fungal and viral pathogens, and, if a match is found, then the subject may be diagnosed as being infected by that pathogen. Unless where excluded explicitly or by context, pathogenic microbes include bacteria, fungi, protozoa, viruses, parasites, and worms. In some embodiments, the nuclease may be programmed with a degenerate recognition sequence representing a known conserved motif coding for a particular gene or genes involved in a molecular pathway of interest. In this way, homologous genes from several species may be enriched for and sequenced simultaneously. In another embodiment, the method may be used for deep sequencing of a host- associated communities (a "microbiome"), with the advantage that the method enables sequencing of all microbial DNA in the sample, not only a subset of the DNA e.g., ribosomal DNA only. Microbes that might be identified using the present methods, compositions and kits include but are not limited to: a plurality of species of Gram (+) bacteria, plurality of species of Gram (−) bacteria, a plurality of species of bacteria in the family *Enterobacteriaceae*, a plurality of species of bacteria in the genus *Enterococcus*, a plurality of species of bacteria in the genus *Staphylococcus*, and a plurality of species of bacteria in the genus *Campylobacter*, *Escherichia coli* (*E. coli*), *E. coli* of various strains such as, K12-MG1655, CFT073, 0157:H7 EDL933, 0157:H7 VT2-Sakai, etc., *Streptococcus pneumoniae*, *Pseudomonas aeruginosa*, *Staphylococcus aureus*, coagulase- negative staphylococci, a plurality of *Candida* species including *C. albicans*, *C. tropicalis*, *C. dubliniensis*, *C. viswanathii*, *C. parapsilosis*, *Klebsiella pneumoniae*, a plurality of *Mycobacterium* species such as *M. tuberculosis*, *M. bovis*, *M. bovis BCG*, *M. scrofulaceum*, *M. kansasii*, *M. chelonae*, *M. gordonae*, *M. ulcerans*, *M. genavense*, *M. xenoi*, *M. simiae*, *M. fortuitum*, *M. malmoense*, *M. celatum*, *M. haemophilum* and *M. africanum*, *Listeria* species, *Chlamydia* species, *Mycoplasma* species, *Salmonella* species, *Brucella* species, *Yersinia* species, etc. Thus, the subject method enables identification of microbes to the level of the genus, species, sub-species, strain or variant of the microbe.

In addition, because the subject method enables sequencing of target sequences of interest, genetic features such as SNPs associated with antimicrobial resistance or susceptibility can be determined. The subject method does not require the culturing or isolation of microbes and thus enables the detection and sequencing of microbial sequences of interest from nucleic acid samples in which they may be at very low abundances.

Methods for extracting total DNA and RNA from various samples, e.g., clinical, forensic, and environmental samples, are well known in the art. Samples include, but are not limited to, skin swab, skin biopsy, saliva, tooth swab, tooth scrapping, cheek swabs, throat swab, sputum, endogastric sample, feces, urine, vaginal, cervical, endocervical, endometrial, nasal swab, lung, organ biopsy, and tissue biopsy. A sample can also be a bodily fluid. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit and urine. In particular embodiments, the sample may be a clinical sample, e.g., a sample collected from a patient. In certain cases, the DNA in these samples may be highly fragmented, e.g., to an average size in the range of 10 bp to 5 kb, e.g., 20 bp to 200 bp and in certain cases may be fragmented using the methods described herein. Methods for extracting total DNA from such samples are well known.

13. APPLICATIONS AND DISEASE STATES

In one application, the method is used to target antibiotic resistance genes for diagnostic purposes. See Examples 5-7, below.

In addition to acquired resistance elements, antimicrobial resistance can also be conferred by a single point mutation in chromosomal genes. Notably, enrichment-plus-NGS can recover SNP data simultaneously with presence/absence data for acquired resistance genes located on mobile genetic elements and these sequences may also be detected and analyzed using enrichment-plus-NGS. These data demonstrate that the method described herein allow individual target genes to be enriched over tens of thousands of times over their abundance when analyzed by NGS alone. These enrichment effects are dependent on the increased proportion of on-target sequences relative to non-target sample sequences and non-sample sequences achieved with this method In addition to acquired resistance elements, antimicrobial resistance can also be conferred by a single point mutation in chromosomal genes. Notably, enrichment-plus-NGS can recover SNP data simultaneously with presence/absence data for acquired resistance genes located on mobile genetic elements. These data demonstrate that the method described herein allow individual target genes to be enriched over tens of thousands of times over their abundance when analyzed by NGS alone. These enrichment effects are dependent on the increased proportion of on-target sequences relative to non-target sample sequences and non-sample sequences achieved with this method.

In addition, the method may be used to detect an RNA virus or a reverse transcribing virus, e.g., reovirus, rotavirus, enterovirus, rhinovirus, hepatovirus, cardiovirus, aphthovirus, poliovirus, parechovirus, erbovirus, kobuvirus, teschovirus, coxsackie, norwalk virus, rubella virus, alphavirus, lymphocytic choriomeningitis virus, dengue virus, hepatitis C virus, yellow fever virus, influenzavirus A, influenzavirus B, influenzavirus C, isavirus, thogotovirus, measles virus, mumps virus, respiratory syncytial virus, Rinderpest virus, canine distemper virus, California encephalitis virus, hantavirus, rabies virus, Ebola virus, Marburg virus, corona virus, astrovirus, borna disease virus, arterivirus, equine arteritis virus, hepatitis E virus, retroviruses (e.g., HIV-1 and HIV-2) and hepatitis B virus.

Disease states may exhibit either the presence of a novel microbe(s), absence of a normal microbe(s), or an alteration in the proportion of microbes. Disease states may also have substantially similar microbial populations as normal states, but with a different microbial function or a different host response to the microbes due to environmental or host genetic factors. For example, recent research has established that disruption of the normal equilibrium between a host and its microbiota, generally manifested as a microbial imbalance, is associated with, and may lead to, a number of conditions and diseases. Examples are provided in WO2018035062A1 (e.g., p. 10, line 11 to p. 11, line 10) which is incorporated herein by reference The method may also be used to detect microbial DNA or RNA sequences and simultaneously detect human DNA or RNA sequences, allowing the study definable sequences from a pathogen and host in the same experiment.

The method may also be used for genotyping. In this case it would target particular sites within a pathogen or other species that can be used to differentiate specific strains or other subpopulations. In the case of infection with multiple subpopulations, or detection of multiple subpopulations in a microbiome or environmental sample, this method, applied either with or without unique molecular identifiers (UMIs) can be used to assess relative amounts of the different subpopulations.

In some embodiments, the method can be used to determine the target sequence of nucleases such as restriction endonucleases, homing endonucleases, and programmable nucleases such as Cas9 or Cpf1. For example, to identify cleavage sites of a particular Cas9 guide RNA combination, a genomic DNA library synthesized with blocked adapters can be treated with the Cas9 and guide RNA to allow selective amplification of sequences containing cleavage sites.

In some embodiments, this method may be used to assess the effectiveness and specificity of particular Cas9 guide RNAs. In this case a library of guide RNAs can be used to direct the digestion of a nucleic acid sample. By comparing the amount of target sequences present after enrichment directed by individual guide RNAs to their amounts in the sample before enrichment, the method can be used to measure the likelihood of an individual guide RNA to allow for digestion.

14. EXAMPLES

14.1 Example 1—General Protocol for Enrichment by Cas9 Digestion Followed by Next-Generation Sequencing This Example provides an exemplary protocol used in the experiments described in Examples 2-7 and is one embodiment of the method described herein.

Reagents

Regents include the rAPID alkaline phosphatase enzyme and buffer which is available from Sigma Aldrich (4898133001). Sodium orthovanadate available from NEB (P0758L). A Cas9 stock solution diluted to 4 uM may be obtained commercially or prepared. Dual guide RNAs at 40 uM targeted to genes or regions of interest are comprised equimolar solutions of crRNA and tracrRNA. A 10 x Cas9 Activity Buffer is made comprising 500 nM Tris ph 8.0, 1 M NaCl, 100 nM $MgCl_2$, 10 nM TCEP. Proteinase K is available from NEB (P8107S). Solid Phase Reversible Immobilization (SPRI) beads may be prepared by known methods. A NEBNext® dA-Tailing Module reagents and NEBNext® Ultra II Ligation Module reagents are available from NEB (E6053L and E7595, respectively). Adaptor (1:100 dilution in Adaptor dilution buffer), USER enzyme, and Q5 master mix may also be purchased from NEB (E7337AA, M5505, and M0544, respectively). Indexing TruSeq i7/i5 barcode primers may be obtained from the UCSF Center for Advanced Technology. Nuclease-free $H_2O$ is available from Ambion. 2100 High-sensitivity dsDNA Bioanalyzer Kit and chips may be obtained from Agilent 5067-462. Qubit hsDNA kit and instrument may be obtained from ThermoFisher Q32854.

Sample DNA

Sample DNA is as described below. Generally 10 picograms to 100 nanograms sample DNA was used.

End-Blocking

The sample DNA is dephosphorylated. For each sample, 10 picograms to 100 nanograms DNA is combined with 2 μl rAPid Alkaline Phosphatase Buffer, 1 μl rAPid Alkaline Phosphatase and nuclease-free $H_2O$ to bring the total volume up to 20 μl. This is incubated at 37° C. for 30 minutes. 1 μl sodium orthovanadate is added to quench the reaction.

Cas9 Treatment

The sample is treated with Cas9. Dual-guide RNAs are prepared by annealing crRNA and tracrRNA at an equimolar amount at 95° C. for 30 seconds, then allowed to cool at room temperature. Cas9 is diluted, if necessary, to 4 uM or other appropriate concentration in 1 x Cas9 activity buffer. For each sample a master mix may be created, comprising (for each sample to be used) 3 μl 10 x Cas9 activity buffer, 2.5 μl 4 μM Cas9, 3 μl 40 μM dual guide RNAs, and 0.5 μl nuclease-free $H_2O$. This 9 μl master mix is added to each 21 μl dephosphorylated DNA sample. Alternatively, these components may be added separately to the individual samples. The Cas9 is thoroughly mixed with the dephosphorylated DNA by pipetting or tapping the tube. The sample is then be incubated at 37° C. for two hours.

Proteinase K Digestion

1 μl proteinase K is then added to each sample, and the sample will incubate at 37° C. for 15 minutes for the proteinase K to inactivate the Cas9.

Proteinase K Removal

The sample will be cleaned up on Solid Phase Reversible Immobilization (SPRI) beads. Clean SPRI beads are equilibrated to room temperature and vortexed well to mix. SPRI beads are added equivalent to 1.7 times the sample volume to each sample tube (e.g., for 31 μl of sample, 53 μl beads will be added). The beads and sample are mixed well by pipetting or tapping the tubes. They are then pulse-spun in a picofuge. The beads and sample incubate for at least 5 min at room temperature, and then are placed on the magnetic rack. Beads are allowed to separate on the magnet for 1-5 minutes, or until the supernatant is clear. While the tubes are kept on the magnet, supernatant is carefully removed and discarded. 200 µl 70% or 80% ethanol is then added. The beads incubate for at least 1 minute and then the ethanol is removed. The above ethanol wash step is repeated. The beads are allowed to air dry for 3-15 minutes. Tubes are removed from magnet and the beads are resuspend in 53 uL nuclease-free $H_2O$. Tubes may be tapped and spun down briefly in a picofuge. DNA is allowed to elute from beads for at least 2 min, and then the tubes are transferred back to magnet. The beads are allowed to separate for at least 2 minutes, and then 50.4 µl of supernatant is collected to clean PCR tubes.

dA Tailing

Next, the digested samples are dA-tailed. 6 µl dA-tailing buffer and 3.6 µl Klenow fragment are added to each 50.4 µl of digested sample. This is mixed and then incubated at 37° C. for 30 minutes, and cooled to 4° C.

Adaptor Ligation

Next, the adaptors are ligated to the digested fragments. The reagents in this step is viscous and may be mixed well. The user should not create a master mix for this step, with the exception of the Ligation Master Mix and Ligation Enhancer, which may be combined and kept at 4° C. for up to 4 hours before using. To each sample add 30 µl NEB Ultra II Ligation Master Mix, 1 µl NEBNext® Ligation Enhancer reagent, and 2.5 µl NEBNext® Adaptor reagent, 1:100 dilution. The sample will be mixed by pipetting up and down several times. The sample will be incubated at 20° C. for 15 minutes in a thermocycler with the heated lid turned off. Then, 3 µl NEB USER Enzyme is added to each sample and mixed well by pipetting up and down several times. The sample is incubated at 37° C. for 15 minutes with the heated lid turned on.

Sample Clean-Up and Removal of Ligase

The sample will be cleaned up on SPRI beads. Clean SPRI beads are equilibrated to room temperature and vortexed well to mix. SPRI beads are added at the same volume as the sample volume to each sample tube (e.g., the sample is at 96.5 µl, so 96.5 µl beads will be added). Nucleic acid is isolated as described above, and 17 uL of water is added during the elution step, of which 15 µl of supernatant is collected to clean PCR tubes.

Optional Library Indexing

In some cases, the library may be indexed, for example, using i5/i7 barcodes and choosing a barcode for each sample. For each sample, 15 µl ligated sample, 10 µl TruSeq barcoded primers, and 25 µl NEBNext® Ultra II 2 x Q5 PCR Master Mix reagent are used. On a thermocycler, the samples are PCR amplified under the following cycling conditions: one cycle of 98° C. for 30 seconds, 16-30 cycles of 98° C. for 10 seconds and 65° C. for 75 seconds, one cycle of 65° C. for 5 minutes, then hold at 10° C.

Next, the sample will be cleaned up on SPRI beads generally as described above. Followed by addition of 22 uL of water during the elution step and collection of 20 µl of supernatant to clean PCR tubes. The samples are analyzed by HS DNA Qubit and the HS DNA Bioanalyzer.

Next Generation Sequencing

The library is analyzed by next-generation sequencing using Illumina MiSeq or NextSeq instruments.

14.2 Example 2—Elimination of the 95 degrees C. incubation affects the fraction of target sequences of interest in the sample following enrichment.

Following enrichment by the method disclosed herein, an enriched sample comprises sequences of interest from the nucleic acid sample ("target sequences"), sequences from the sample that are not sequences of interest ("non-target sample sequences), as well as exogenous sequences ("non-sample sequences").

In the method, nucleic acid samples are end-blocked by dephosphorylation, purified on a column to remove the phosphatase, incubated with complexed Cas9 and guide RNAs to digest the sample at sequences of interest, and then treated with proteinase K to remove Cas9. Using conventional methods, proteinase K is inactivated by treatment at high temperature, e.g., an incubation at 95° C. for five minutes. We tested whether the elimination of the 95° C. incubation affects the fraction of target sequences of interest in the sample following enrichment. In addition, we altered the amount of Cas9 added for every nanogram of sample nucleic acid.

DNA was isolated from a dried blood spots containing *Plasmodium*. The method of enrichment was performed for a set of antimicrobial resistance genes with and without a five minute incubation at 95° C. to inactivate proteinase K. Following enrichment, we performed next-generation sequencing and measured the percentage of on-target.

Enrichment with the 95° C. incubation resulted in a 51-fold increase in the percentage of reads mapping to target sequences of interest over an unenriched (no Cas9 added) control. Enrichment without the 95° C. incubation resulted in a 700-fold increase in the percentage of reads mapping to target sequences of interest over the unenriched (no Cas9 added) control (FIG. 2A).

14.3 Example 3: Treatment with very Low Concentrations of Cas9

We investigated the effect of treatment with very low concentrations of Cas9 in protocols without a 95° C. proteinase K inactivation step. We performed enrichment of the Plasmodium AMR genes using 20 pmol Cas9/ng sample DNA or 0.4 pmol Cas9/ng sample DNA. See FIG. 2A and 2B. We found that using the lowered concentration of Cas9 resulted in an 824-fold increase in the percentage of reads mapping to target sequences of interest over an unenriched (no Cas9) control (FIG. 2B). An average of two samples and the standard deviation between them are shown (FIG. 2B).

In addition, the percentage of non-sample and non-target sample reads dropped to less than 20% of the library following enrichment. See FIG. 2B.

14.4 Example 4—Enrichment is Observed with as Little as 0.0032 Picomole Cas9 per ng Sample DNA is Needed for Enrichment We varied the amount of Cas9 with respect to the amount of DNA in the starting sample using a guide RNA library targeting Gram-positive AMR genes for enrichment. We determined that with as little as 0.0032 picomole Cas9 per nanogram of DNA in the sample, the method of enrichment described herein followed by next-generation sequencing yielded at least 10 reads per million (rpM) for each target AMR gene (FIG. 3).

Figure 3:
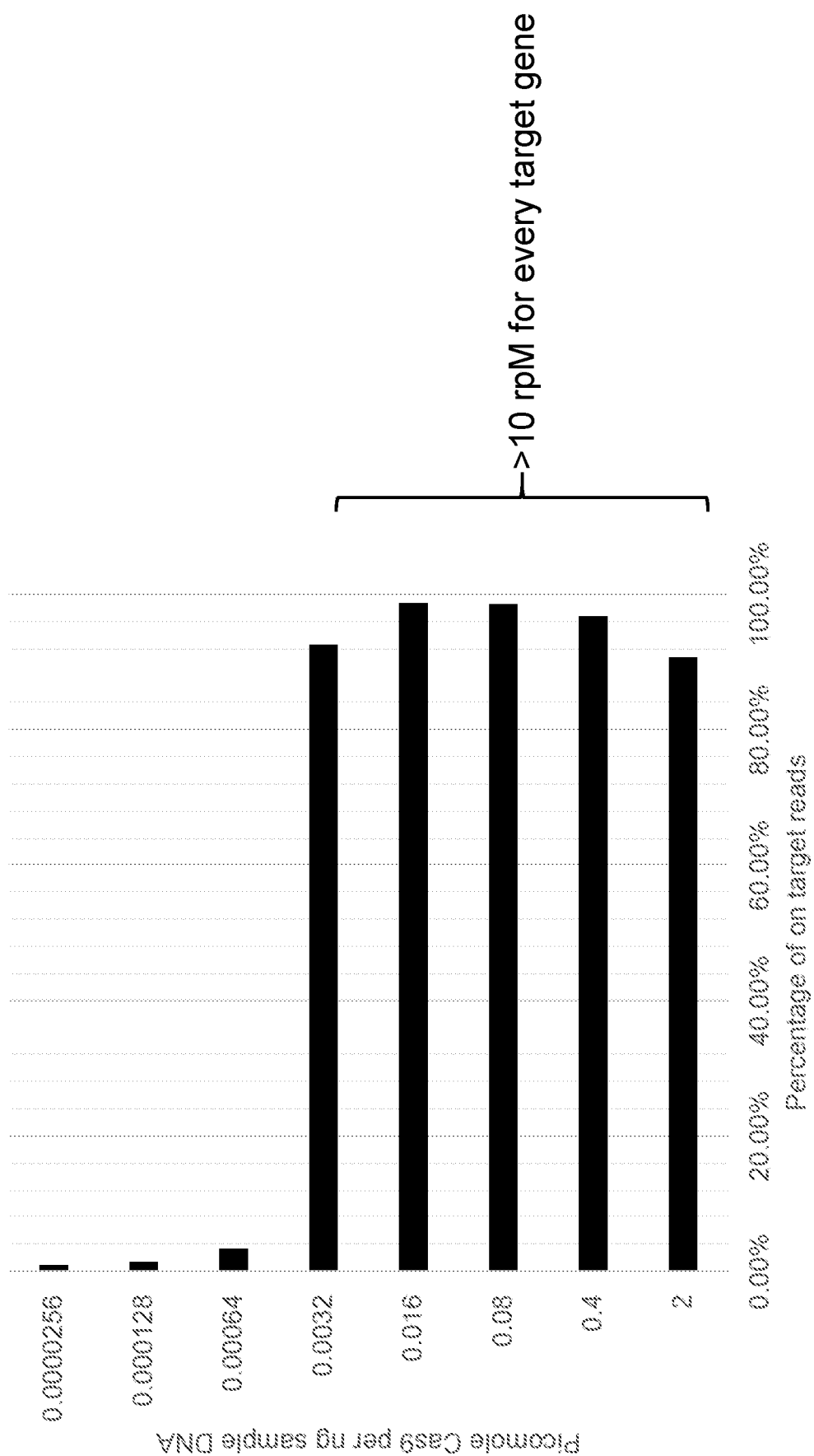
FIG. 3 shows the relationship between starting concentration of Cas9 and the fraction of on-target reads.

With Cas9 at a range of concentrations from 0.0032 picomole/ng sample DNA to 2 pmole/ng sample DNA the method of enrichment described herein yielded at least 10 rpM for each target gene, and on-target reads represented more than 90% of the final sequencing library (FIG. 3).

14.5 Example 5—Enrichment of Antimicrobial Resistance Genes from Cultured Isolates of Staphylococcus aureus One of the applications of the method described herein is the enrichment of sequences of interest from bacterial genomic DNA samples. We designed a library of guide RNAs to target Cas9 to antimicrobial resistance (AMR) gene sequences from Gram-positive bacteria, and used the method described herein to enrich for AMR genes from clinical isolates of the bacterial pathogen *Staphylococcus aureus*. Methicillin resistant *S. aureus* (MRSA) is a drug resistant infection, and antimicrobial susceptibility information is crucial for implementing targeted and effective therapeutic interventions for drug resistance infections.

DNA was isolated from six clinical *S. aureus* isolates. Isolated DNA was sequenced with traditional next-generation sequencing (NGS) with or without enrichment for antimicrobial resistance (AMR) gene sequences by the enrichment method described herein (referred to in the figure as "enrichment-plus-NGS"). Each was sequenced to a depth greater than 0.5 M reads. Briefly, for enrichment-plus-NGS, 5 ng of DNA was end-blocked with phosphatase and treated with Cas9 complexed to the guide library. The resulting fragments were dA-tailed to create single A 3' overhangs to allow ligation to adapter with single T overhangs. The remaining library preparation steps were identical to those used in the standard NEBNext Ultra II ligation-based kit, which includes adapter ligation followed by amplification using custom dual unique index primers. The libraries were amplified, enriching for adapted fragments, pooled, size selected using gel electrophoresis on a Blue Pippin instrument, and sequenced on an Illumina NextSeq. For NGS-only control libraries, 5 ng of the same input DNA was prepared with the NEBNext Ultra II FS DNA-Seq kit and indexed, pooled, size selected and sequenced in the same manner.

Data were demultiplexed, quality filtered with PriceSeq-Filter (Ruby et al., 2013, *Genomes Genetics* 3), aligned to the 125 targeted *S. aureus* genes using Bowtie2, and further analyzed with custom python scripts. All samples were analyzed in three independent experiments, and unless otherwise noted, all reported data represents average reads per million (rpM).

In all cases, NGS of these isolates identified the 9 chromosomal genes in our target set, along with 0-4 acquired resistance genes consistent with phenotypic resistance data. See TABLE 1 ("Flash" is enrichment-plus-NGS" and "NGS" is NGS without enrichment. TABLE 1 shows the proportion of targeted genes present following enrichment by the method described herein followed by next-generation sequencing, versus next-generation sequencing-alone for six Staphylococcus aureus isolates. All these genes were enriched. On average, 87.5% of reads mapped to these genes, (indicating a background of non-Cas9-derived reads of only 12.5%) compared to 0.10% mapping to these genes with NGS alone. In all enrichment-plus-NGS samples a sequencing depth of 3000 reads was sufficient to recover 10 or more reads per gene for 100% of targeted genes. For NGS alone, this depth would not yield 10 reads per gene for any targets; over 300,000 reads would be needed to achieve 10 reads for 100% of targets.

| Name | Method | chromosomal | | | | | | | |
|---|---|---|---|---|---|---|---|---|---|
| | | pgsA | gyrA | cls | gyrB | mprF | parC | rpoB | rpoC |
| isolate 1 average | FLASH | 3.74 | 4.99 | 2.85 | 2.28 | 1.38 | 6.02 | 8.67 | 5.37 |
| isolate 2 average | FLASH | 6.98 | 10.82 | 5.36 | 6.09 | 3.70 | 10.11 | 15.32 | 9.15 |
| isolate 3 average | FLASH | 4.75 | 5.16 | 2.88 | 2.43 | 1.51 | 6.09 | 7.18 | 5.08 |
| isolate 4 average | FLASH | 6.28 | 11.55 | 6.79 | 4.13 | 3.21 | 11.30 | 17.32 | 7.12 |
| isolate 5 average | FLASH | 3.22 | 11.16 | 3.83 | 3.65 | 2.18 | 5.69 | 18.37 | 6.25 |
| isolate 6 average | FLASH | 1.49 | 13.92 | 2.94 | 7.61 | 2.67 | 6.08 | 36.19 | 5.68 |
| isolate 1 average | NGS | 0.01 | 0.05 | 0.03 | 0.03 | 0.03 | 0.03 | 0.07 | 0.05 |
| isolate 2 average | NGS | 0.01 | 0.04 | 0.02 | 0.02 | 0.02 | 0.02 | 0.05 | 0.04 |
| isolate 3 average | NGS | 0.01 | 0.04 | 0.02 | 0.03 | 0.02 | 0.02 | 0.06 | 0.05 |
| isolate 4 average | NGS | 0.01 | 0.04 | 0.02 | 0.02 | 0.02 | 0.02 | 0.05 | 0.04 |
| isolate 5 average | NGS | 0.00 | 0.02 | 0.01 | 0.01 | 0.01 | 0.01 | 0.03 | 0.02 |
| isolate 6 average | NGS | 0.00 | 0.06 | 0.02 | 0.03 | 0.02 | 0.02 | 0.09 | 0.04 |

-continued

| Name | Method | parE | mecA | mecR1 | ErmC | dfrG | non-targeted genes |
|---|---|---|---|---|---|---|---|
| isolate 1 average | FLASH | 5.64 | 4.26 | 6.26 | 43.16 | 0.00 | 5.36 |
| isolate 2 average | FLASH | 12.66 | 5.93 | 7.67 | 0.10 | 0.00 | 6.10 |
| isolate 3 average | FLASH | 6.22 | 4.43 | 5.54 | 41.45 | 0.44 | 6.83 |
| isolate 4 average | FLASH | 11.47 | 7.59 | 8.08 | 0.06 | 0.00 | 5.11 |
| isolate 5 average | FLASH | 10.03 | 0.05 | 0.03 | 16.13 | 0.00 | 19.40 |
| isolate 6 average | FLASH | 5.91 | 0.05 | 0.05 | 0.65 | 0.00 | 16.76 |
| isolate 1 average | NGS | 0.03 | 0.02 | 0.01 | 0.13 | 0.00 | 99.52 |
| isolate 2 average | NGS | 0.02 | 0.02 | 0.01 | 0.00 | 0.00 | 99.72 |
| isolate 3 average | NGS | 0.02 | 0.02 | 0.01 | 0.11 | 0.00 | 99.60 |
| isolate 4 average | NGS | 0.02 | 0.02 | 0.01 | 0.00 | 0.00 | 99.73 |
| isolate 5 average | NGS | 0.01 | 0.00 | 0.00 | 0.03 | 0.00 | 99.87 |
| isolate 6 average | NGS | 0.01 | 0.00 | 0.00 | 0.00 | 0.00 | 99.72 |

14.6 Example 6—Enrichment of Antimicrobial Resistance Genes from Respiratory Fluid Metagenomic Samples Demonstrates Hundreds to Thousands-Fold Enrichment of the Target Gene mecA Another application of the method described herein is the enrichment of sequences from metagenomic samples such as clinical samples. Indeed, the enrichment achievable with the method described herein is of particular use for complex samples such as clinical samples in which sequences of interest may be low abundance. We assessed the performance of enrichment-plus-NGS for detecting Gram-positive bacterial AMR gene targets directly from six clinical samples from human subjects (three RNA and three DNA). For each sample, 25 ng of DNA or cDNA (converted from RNA using random primers with the Nugen Ovation® v.2 kit) was subjected to enrichment-plus-NGS or NGS alone following the protocol described above. Data were aligned to our set of 125 targeted Gram-positive genes using Bowtie2. All samples were prepared in triplicate.

14.6.1 Methicillin-Resistant MRSA Pneumonia

Figure 4:
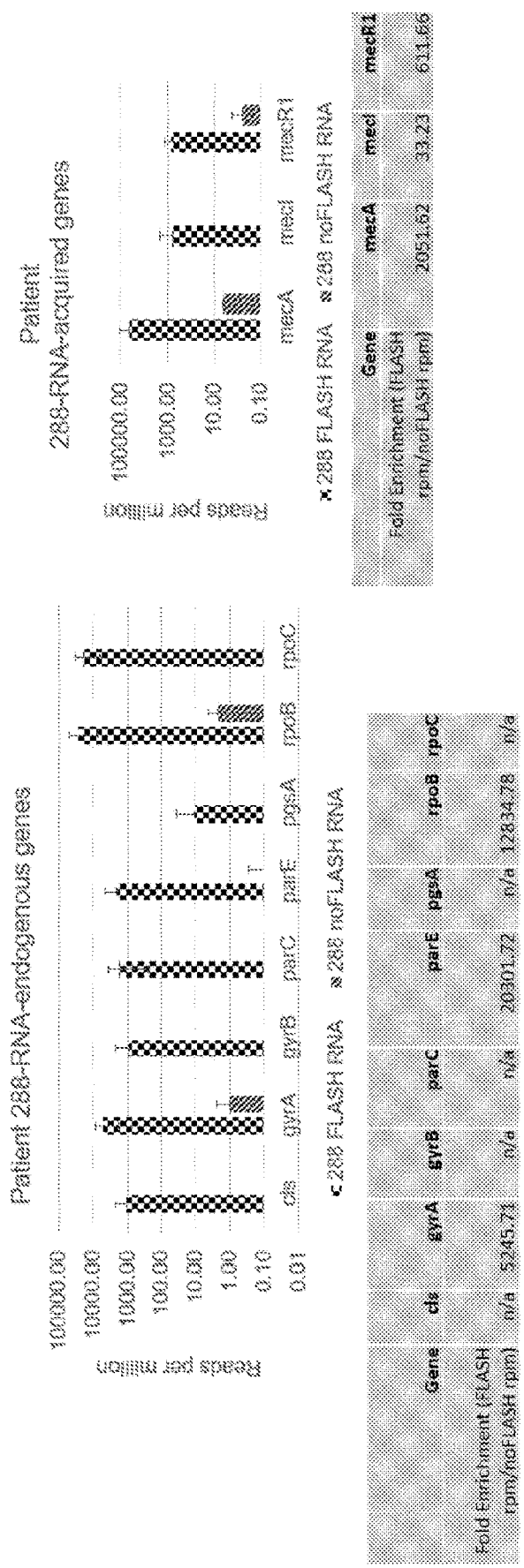
FIGS. 4, 5 and 6 show reads per million for targeted gene in clinical samples detected with NGS-alone and enrichment-plus-NGS.

One human subject (patient 288) was hospitalized for methicillin-resistant Staphylococcus aureus (MRSA) pneumonia. Culture-based susceptibility testing on an isolate grown from respiratory fluid revealed resistance to penicillin, erythromycin and methicillin. Enrichment-plus-NGS of RNA extracted from modified bronchoalveolar lavage (mBAL) identified over 20,000 rpM to mecA, which confers methicillin resistance, a 1000-fold enrichment over NGS alone. FIG. 4 show reads per million for each targeted gene in the clinical sample detected with NGS-alone and enrichment-plus-NGS.

14.6.2 Methicillin- and Sulfonamide-Resistant MRSA Pneumonia

Figure 5:
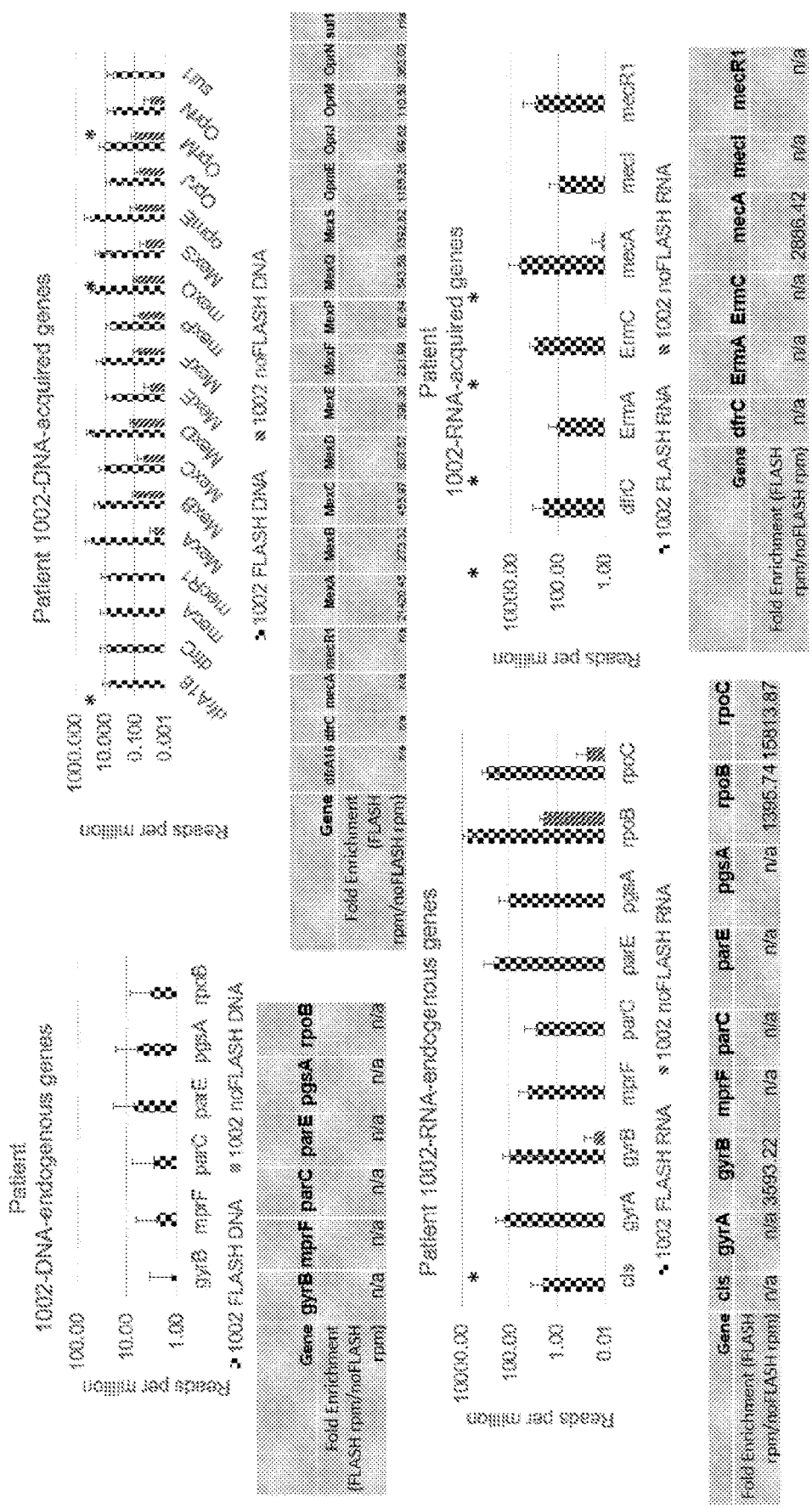

Enrichment-plus-NGS of tracheal aspirate (TA) from a second human subject (patient 1002), who was admitted with fatal MRSA pneumonia, identified mecA and sul1, conferring resistance to methicillin and sulfonamides, respectively (FIG. 5). Here mecA is enriched about 450-fold in the DNA experiment and over 2850-fold in the RNA experiment. Enrichment-plus-NGS identified a single nucleotide polymorphism in gyrA known to confer quinolone resistance, concordant with phenotypic results. Both DNA and RNA were examined for this patient. There were some targets detected in DNA but not in RNA (such as dfrA6 and sul1), likely representing genes not expressed in this context. Notably, other targets were detected in RNA only (such as ErmA and ErmC). These may be genes that are below the limit of detection for DNA, but are enriched in RNA due to high expression levels.

14.6.3 Vancomycin-Resistant Enterococcus faecium (VRE)

Figure 6:
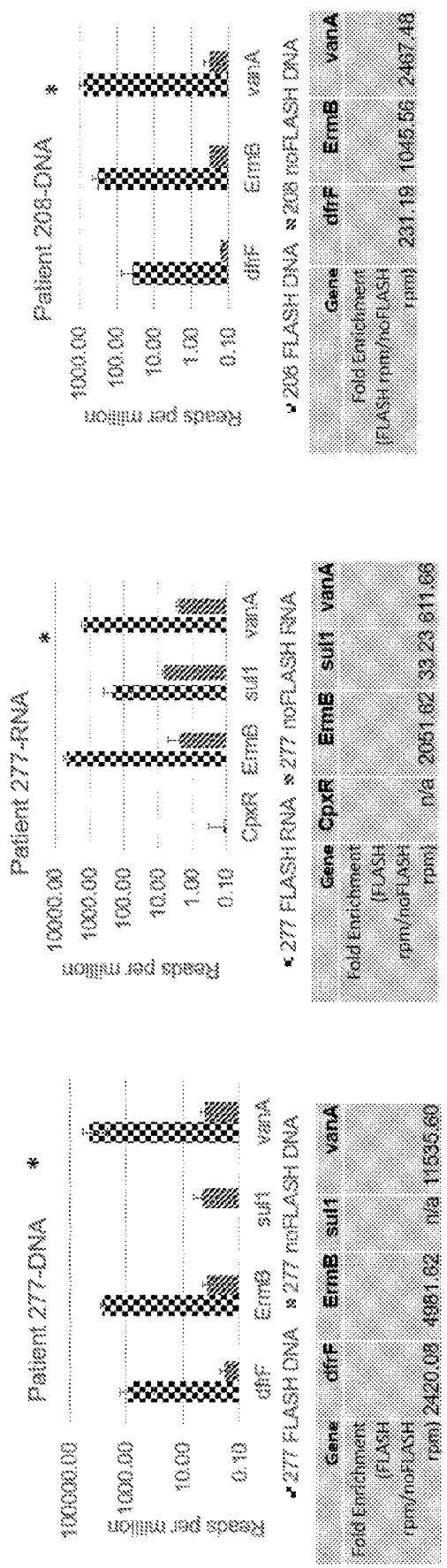

Vancomycin-resistant Enterococcus faecium (VRE) was identified by culture in another human subject (patient 277). Enrichment-plus-NGS of DNA and RNA from mini-bronchial alveolar lavage (mBAL) identified the vanA gene, which confers vancomycin resistance. Resistance to macrolides and trimethoprim-sulfamethoxazole (TM P-SMZ) are widespread in Enterococci and thus identification of ErmB, dfrF and sul1, associated with resistance to macrolides and TMP-SMZ, respectively, was not surprising. Enrichment-plus-NGS enhanced detection of these AMR genes over NGS alone by as much as three orders of magnitude. See FIG. 6.

14.6.4 Vancomycin-Resistant Enterococcus faecium (VRE)

Another human subject (patient 208) (FIG. 6) was admitted for VRE bacteremia. Enrichment-plus-NGS identified vanA as well as ErmB and dfrG with enrichment of two to three orders of magnitude. See FIG. 6.

14.7 Example 7—Detecting Plasmodium Antimicrobial Resistance genes from Dried Blood Spots We designed a library of guide RNAs to target Cas9 to antimicrobial resistance (AMR) gene sequences from *Plasmodium*, the microbial eukaryote that causes malaria in human subjects. Dried blood spots representing three different mixtures of the *Plasmodium falciparum* strains U659, HB3 and D10 were prepared by spotting 20 µL of blood containing 10,000 parasites/µL onto filter paper. DNA was subsequently extracted and amplified by Selective Whole Genome Amplification (sWGA) using custom primers (Oyola et al., 2016, Malaria J. 15:597). One hundred ng of DNA from each sample was subjected to enrichment-plus-NGS in the manner described above, using the *P. falciparum* guide RNA set. This procedure was repeated for three independent sWGA reactions (from either two or three blood spots) from each of three different mixtures, as well as each of the three strains alone. We also sequenced sWGA-amplified mixed-strain blood spots without enrichment to assess SWGA amplification of the regions containing the enrichment targets. Each dataset consisted of at least 2 M PE150 reads. Since PE150 sequencing could not resolve the number of repeats present in any of the microsatellite windows, we re-sequenced the same libraries at SE270 (single end 270). Reads were aligned to the Pf3D7 genome (PlasmoDB version 28) using Bowtie2 and further analysis was done using custom python and R scripts.

Figure 7:
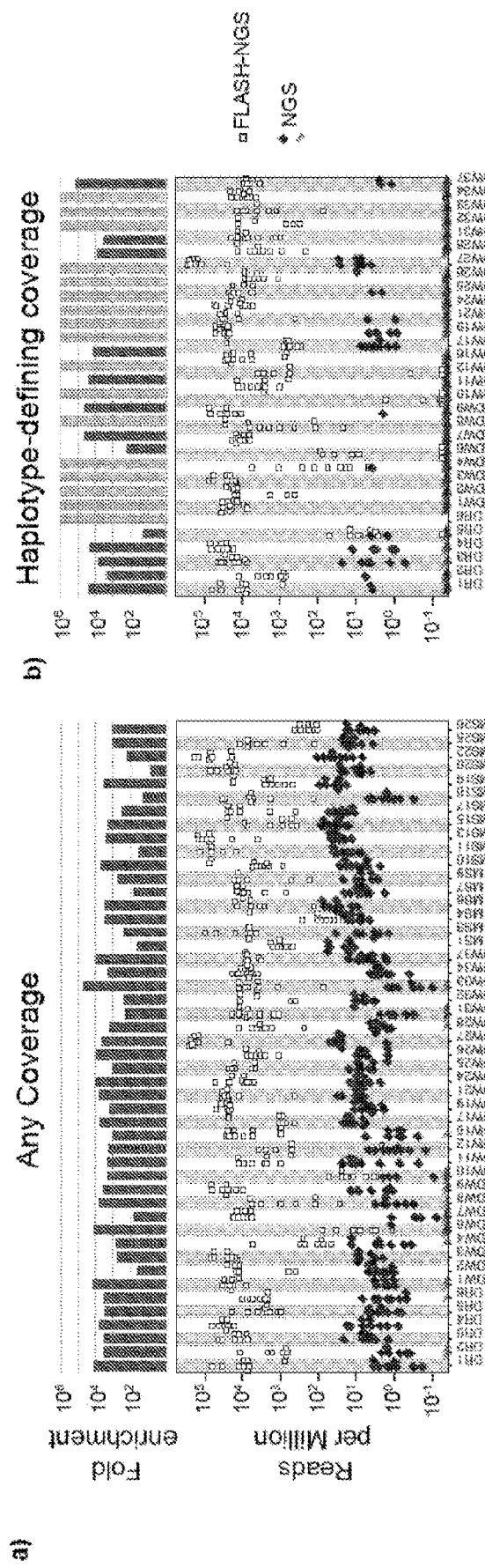
FIG. 7 shows the results of FLASH on dried blood spots. Dried blood spots (DBSs) from malaria lab strains were sequenced using either NGS or enrichment-plus-NGS. Reads per million and fold-enrichment are plotted for each of multiple samples

For the triple strain samples, the 48 windows targeted were enriched from 8-fold to 50,000-fold over traditional NGS when combining all enrichment-plus-NGS experiments from all strain mixtures (n=9, three replicates each of three different strain mixes) (FIG. 7, left panel). When considering only read pairs in which all haplotype-defining SNPS in a particular window were sequenced (FIG. 7, right panel), fold enrichment cannot be calculated for most windows as NGS reads meeting this criterion did not occur at this read depth.

14.8 Example 8—Assessment of Endonuclease-DNA Ratio

An exemplary approach to determining the programmable endonuclease/DNA ratio for use in the present method, is described in this example. As noted above, the enrichment-plus-NGS methods described herein use a small quantity of sample DNA (e.g., 100 nanograms of less) and a small amount of endonuclease (10 pmole/ng). In one approach a stock solution of endonuclease is mixed with a set of guide RNAs, guide DNAs or any other components necessary for programming the new nuclease. The guides should be designed to target sequences known to be present in a sample of interest. The endonuclease and guide nucleic acids are maintained under conditions (e.g., heating, cooling and mixing) that cause the nuclease and the guides or other components to form a complex. A dilution series (e.g., a 2-fold or 10-fold dilution series) of the nuclease/guide complex down to a very low concentration (for example, below 100 pM) and an enrichment-plus-NGS experiment is carried out as described herein (e.g., without exposure to elevated temperature) by adding each one of these dilution series nuclease/guide mixtures to an appropriate amount of phosphatase-blocked target DNA, such as 25 ng.

An adaptor is ligated to the resulting ligatable ends of endonuclease-generated fragments. The adaptor ligation can include dA (or dC, dG, or dT) tailing if the nuclease creates a blunt end or after treatment of an endonuclease generated a sticky end, then either use a polymerase to generate a blunt end and then proceed with dA tailing (or dC, dG or dT tailing) and adapter ligation, or else proceed with ligation with an adapter that has sticky ends that base pair with the ends created by the nuclease. The adapter-ligated samples are amplified and sequenced. Sequencing read alignment tools (such as bowtie2, gsnap or STAR) are used to determine what fraction of reads obtained for each sample map to the targeted sequences. The nuclease concentration corresponding to the sample with the highest fraction of reads mapped to the target sequences is the optimal concentration.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of sample analysis, comprising:
   (a) providing a sample comprising a plurality of end-blocked polynucleotides;
   (b) digesting the sample with one or more defined nucleic acid-directed endonucleases that target one or more sequences of interest to produce a digested sample of polynucleotide fragments, wherein one or more of the fragments in the digested sample comprise:
   one or more sequences of interest and
   at least one ligatable end that has been generated by endonuclease cleavage;
   (c) enriching for fragments that contain the one or more sequences of interest, wherein the one or more sequences of interest are enriched greater than 55 times their relative abundance in the sample, thereby generating an enriched sample; and
   (d) analyzing the enriched sample,
   wherein
   (i) in step (a), a quantity of the end-blocked polynucleotides in the sample is 10 picograms to 100 nanograms, and
   (ii) in step (b), an amount of at least one of the one or more defined nucleic acid-directed endonucleases is 0.0032 pmole to 2 pmoles per nanogram of the end-blocked polynucleotides.

2. The method of claim 1, wherein the method comprises ligating an adaptor to the at least one ligatable end generated by step (b).

3. The method of claim 2, wherein the adaptor comprises capture moiety and the enriching is done by binding the capture moiety to a support, and washing away unbound nucleic acid.

4. The method of claim 2, wherein digestion of (b) creates fragments that comprise ligatable endonuclease cleavage sites on each end, and the method comprises ligating adaptors to each end of the fragments, thereby generating ligated fragments.

5. The method of claim 4, wherein the enriching comprises amplifying the ligated fragments using primers that hybridize to the adaptors, or complements thereof.

6. The method of claim 2 wherein the one or more defined nucleic acid-directed endonucleases comprises a CRISPR-associated protein (Cas).

7. The method of claim 6 wherein the Cas is a Cas9.

8. The method of claim 6 wherein the Cas is a Cas12.

9. The method of claim 2, wherein the sample comprises DNA from at least two organisms.

10. The method of claim 9, wherein the at least two organisms comprise a mammal and a pathogen.

11. The method of claim 10, wherein the pathogen is a virus, a bacterium, or a fungus.

12. The method of claim 9, wherein the at least two organisms comprise a mammal and a microbiome.

13. The method of claim 1, wherein
in steps (b) and (c) the sample is not exposed to an elevated temperature.

14. A method comprising:
providing a sample comprising a plurality of end-blocked polynucleotides; separately digesting
a first portion of the sample with a first one or more defined nucleic acid-directed endonucleases that target a first one or more sequences of interest to produce a first digested sample of polynucleotide fragments, wherein one or more of the fragments in the first digested sample comprise the first one or more sequences of interest and at least one first ligatable end that has been generated by endonuclease cleavage of the first portion of the sample;
a second portion of the sample with a second one or more defined nucleic acid-directed endonucleases that target a second one or more sequences of interest to produce a second digested sample of polynucleotide fragments, wherein one or more of the fragments in the second digested sample comprise the second one or more sequences of interest and at least one second ligatable end that has been generated by endonuclease cleavage of the second portion of the sample, and wherein at least some of the fragments in the first digested sample overlap with at least some of the fragments in the second digested sample;
enriching for fragments that comprise the first and the second one or more sequences of interest, thereby generating enriched sequences;
sequencing the enriched sequences to produce a plurality of sequence reads; and
assembling overlapping sequence reads, thereby obtaining a contiguous sequence of a first sequence of interest and a second sequence of interest,
wherein
(i) a quantity of the end-blocked polynucleotides in the sample is 10 picograms to 100 nanograms, and
(ii) an amount of at least one of the one or more defined nucleic acid-directed endonuclease is 0.0032 pmole to 2 pmoles per nanogram of the end-blocked polynucleotides.

* * * * *

UNITED STATES PATENT AND TRADEMARK OFFICE
CERTIFICATE OF CORRECTION

PATENT NO. : 11,987,837 B2
APPLICATION NO. : 17/265499
DATED : May 21, 2024
INVENTOR(S) : Emily D. Crawford and Jenai Quan It is certified that error appears in the above-identified patent and that said Letters Patent is hereby corrected as shown below:

On the Title Page (Other Publications)
Column 2, item (56) References Cited:
Delete "BioRixv," and
Insert -- BioRxiv, --.

Column 2, item (57) Abstract:
Delete "endblocked," and
Insert -- end-blocked, --.

In the Specification

In Column 1, Line 15:
Delete "Aug. 6, 2018," and
Insert -- Aug. 6, 2019, --.

In the Claims

In Column 25, Line 12:
In Claim 13, delete "(c)" and
Insert -- (c), --.

Signed and Sealed this
Sixteenth Day of July, 2024

Katherine Kelly Vidal
*Director of the United States Patent and Trademark Office*